(12) United States Patent
Miyachi et al.

(10) Patent No.: US 7,176,204 B2
(45) Date of Patent: Feb. 13, 2007

(54) SUBSTITUTED CARBOXYLIC ACID DERIVATIVES

(75) Inventors: Hiroyuki Miyachi, Kazo (JP); Kouji Murakami, Oyama (JP)

(73) Assignee: Kyorin Pahrmaceutical Co., Ltd., Tokyo (JP)

( * ) Notice: Subject to any disclaimer, the term of this patent is extended or adjusted under 35 U.S.C. 154(b) by 162 days.

(21) Appl. No.: 10/433,153

(22) PCT Filed: Dec. 4, 2001

(86) PCT No.: PCT/JP01/10564

§ 371 (c)(1),
(2), (4) Date: May 30, 2003

(87) PCT Pub. No.: WO02/46161

PCT Pub. Date: Jun. 13, 2002

(65) Prior Publication Data

US 2005/0101521 A1   May 12, 2005

(30) Foreign Application Priority Data

Dec. 5, 2000  (JP) .............................. 2000-369370
Aug. 28, 2001 (JP) .............................. 2001-257390

(51) Int. Cl.
*A61K 31/50*   (2006.01)
*A61K 31/497*  (2006.01)
*C07D 211/72*  (2006.01)
*C07D 213/72*  (2006.01)

(52) U.S. Cl. .................. 514/252.03; 514/352; 514/354

(58) Field of Classification Search ................ 546/309, 546/335, 297, 298, 300; 514/349, 350, 351, 514/252.03, 352, 354; 544/238
See application file for complete search history.

(56) References Cited

U.S. PATENT DOCUMENTS 6,329,372 B1 * 12/2001 Head et al. .................. 514/241

FOREIGN PATENT DOCUMENTS

| EP | 881219 | 12/1998 |
|----|--------|---------|
| JP | 51-136646 | 11/1976 |
| JP | 51149240 | * 12/1976 |
| WO | 97/25042 | 7/1997 |
| WO | 9725042 | * 7/1997 |
| WO | 9736579 | * 7/1997 |
| WO | 97/32863 | 9/1997 |
| WO | 97/36579 | 10/1997 |
| WO | 00/75103 | 12/2000 |
| WO | 01/14349 | 3/2001 |
| WO | 01/14350 | 3/2001 |
| WO | 01/21578 | 3/2001 |
| WO | 01/25181 | 4/2001 |
| WO | 0125181 | * 4/2001 |

OTHER PUBLICATIONS

Proc. Natl. Acad. Sci., 1992, 89, 4653.*
Endocrinology, 1995, 137, 354.*
Proc. Natl. Acad. Sci., 1999, 96, 7473.*
J. Lipid Res., 1997, 37, 907.*
Ca 124:342873, "Preparation of guanidinobenzoate esters as serine protease inhibitors", Hashiguchi et. al., 1996.*
Database Caplus 'Online!, AN 2002:793403, XP-002306640, WO 02/080899, Oct. 17, 2002.

* cited by examiner

*Primary Examiner*—Thomas McKenzie
*Assistant Examiner*—Binta Robinson
(74) *Attorney, Agent, or Firm*—Oblon, Spivak, McClelland, Maier & Neustadt, P.C.

(57) ABSTRACT

Novel substituted carboxylic acid derivatives which bind as ligands to human peroxisome proliferator activated receptor (PPAR) to activate the receptor and thereby exhibit potent effects of decreasing neutral fat, cholesterol, and blood sugar; and a processes for preparing the derivatives. Specifically, substituted carboxylic acid derivatives represented by general formula (1), and pharmaceutically acceptable salts and hydrates of the derivatives, and a processes for preparing the derivatives, the salts, or the hydrates

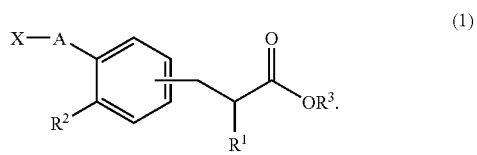

(1)

20 Claims, No Drawings

SUBSTITUTED CARBOXYLIC ACID DERIVATIVES

TECHNICAL FIELD

The present invention relates to substituted carboxylic acid derivatives, effective for therapeutic drugs for metabolic diseases such as hyperlipemia, obesity and diabetes as agonists of human peroxisome proliferator-activated receptor (abbreviated as PPAR), in particular, as agonists for human PPARα isoform, their addition salts, processes for preparing them, and medicinal compositions containing these compounds.

BACKGROUND TECHNOLOGIES

Peroxisome proliferator-activated receptor (PPAR) is a ligand-dependent transcription factor that belongs to nuclear receptor superfamily such as steroid receptor, retinoid receptor, thyroid receptor, etc. Three isoforms (α type, δ (or β) type and γ type) with different histological distribution have been identified hitherto in human and various animal species (Proc. Natl. Acad. Sci., 1992, 89, 4653). Thereamong, PPARα is distributed in the liver, kidney, etc. with high catabolic capacity for fatty acids and, in particular, high expression is recognized in the liver (Endocrinology, 1995, 137, 354), positively or negatively controlling the expressions of genes relevant to the metabolism and the intracellular transport of fatty acids (e.g. acyl CoA synthetic enzyme, fatty acid-binding protein and lipoprotein lipase) and apolipoprotein (AI, AII and CIII) genes relevant to the metabolisms of cholesterol and triglyceride. PPARδ is expressed ubiquitously in the tissues of organisms, including nerve cells. At present, the physiological significance of PPARδ is unclear. PPARγ is highly expressed in the adipocytes and involved the differentiation of adipocytes (J. Lipid Res., 1996, 37, 907). In this way, each isoform of PPAR plays specific functions in the particular organs and tissues.

Moreover, it is reported that a knock-out mouse of PPARα exhibits hypertriglyceridemia with ageing and becomes obesity mainly by increasing the white adipose tissues (J. Biol. Chem., 1998, 273, 29577, J. Clin. Invest., 1998, 102, 1083, Proc. Natl. Acad. Sci., 1999, 96, 7473), hence it is strongly suggested that the PPARα is playing an important role in the regulations of homeostasis of lipids (cholesterol and triglyceride) and glucose in blood and energy balance.

Now, fibrate type drugs have been widely used hitherto as the therapeutic drugs for hyperlipidemia, in particular, therapeutic drugs for hypertriglyceridemia and, as the mechanism of these fibrate type drugs, the activation of PPARα is reported (J. Lipid Res., 1996, 37, 907). In addition, it is reported that the fibrate type drugs inhibit the increases in body weight and weight of adipose tissues and further normalize the glucose tolerance capacity in insulin-resistant animal models (J. Biol. Chem., 2000, 275, 16638, Biochem. Biophys. Res. Commn., 2000, 271, 445), hence it is shown that PPARα takes part also in the improvement in insulin resistance.

However, fibrate type drugs exhibit only weak activating function of PPARα and they are never satisfied in the aspect of potency. Moreover, with respect to the fibrate type drugs, various adverse effects, such as gastrointestinal injury, anthema, headache, hepatic disorder, renal disorder and biliary calculus are reported. This cause is considered to be due to various nonspecific functions exhibited by fibrate type drugs, hence the development of a therapeutic drug for metabolic diseases with specific mechanism is desired.

With respect to the activators of PPARγ, thiazolidinedione derivatives such as Pioglitazone and Rosiglitazone are launched in the market, but, with these drugs, hepatopathy and cardiac disorders are reported, hence it is said that sufficient caution and strict management are required on the use. For this reason, it is the present situation that drugs satisfiable clinically enough in both aspects of their therapeutic effects and adverse effects such as toxicity are not still obtained.

With respect to the activators of PPARδ, compounds of L-165041 and GW501516 are known, but they are limited to the introduction in the literatures and come not to be launched in the market.

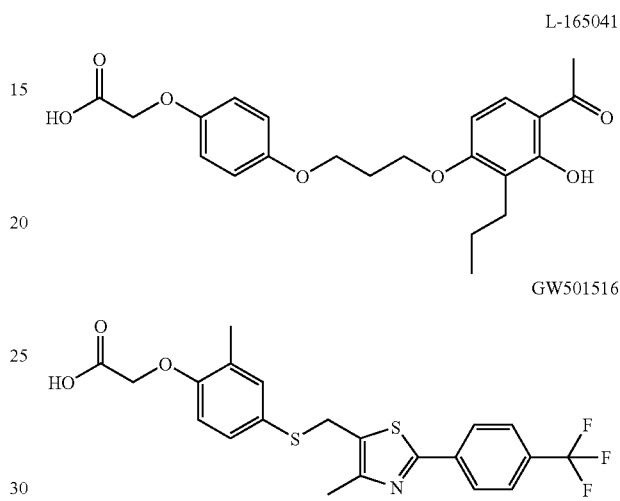

Then, when considering the relevance between the role of nuclear receptor of PPARα on the regulatory mechanism of lipid metabolism and the pathologies of hyperlipidemia, obesity and diabetes, if a compound that binds directly to as a ligand of PPARα, in particular, human PPARα and is capable of activating human type PPARα could be created, the medicinal use would be expected as a therapeutic drug for metabolic diseases provided with very specific mechanism.

For compounds having an affinity to PPARα as ligands of PPARα, eicosanoids in HETE (hydroxyeicosatetraenoic acid) group produced via oxidation with cytochrome P-450, in particular, 8-HETE, 8-HEPE, etc. are reported in addition to $LTB_4$ being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

On the other hand, as compounds with similar structure to the inventive substituted carboxylic acid derivatives, compounds shown below, etc. are reported.

As α-substituted phenylpropionic acid derivatives with blood glucose-decreasing action and lipid-decreasing action, in Japanese Unexamied Patent Publication No. Hei 11-158144 (SS Pharmaceutical Co., Ltd.), compounds represented by a general formula (A)

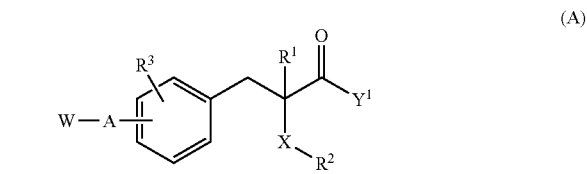

(wherein W denotes a (substituted) lactam ring, A denotes an alkylene group or alkyleneoxy group, X denotes O, S, NH or $CH_2$, $Y^1$ denotes an amino group, hydroxyl group or alkoxy group, $R^1$ denotes H, alkyl group or the like, $R^2$ denotes an alkyl group, phenyl group or the like, and $R^3$ denotes an alkyl group, alkoxy group or the like) are reported.

However, these compounds have different structure from that of the inventive compounds in the points that carbonyl group or amide group is not contained in A being connecting portion and that lactam ring is contained in W being end substituent, and it is not described that these compounds have the binding activity to human PPARα and the transcription-activating function.

As compounds with blood glucose-lowering action, in International Publication No. WO98/28254 (Nippon Chemiphar Co., Ltd.), compounds represented by a general formula (B)

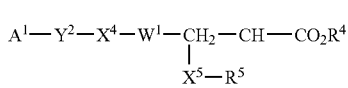

(B)

(wherein $A^1$ denotes an aryl group which may have substituents or heterocycle group, $Y^2$ denotes an alkylene chain with carbon atoms of 1 to 5, $X^4$ denotes a bond hand, oxygen atom or sulfur atom, $W^1$ denotes a naphthalene ring which may have substituents, quinoline ring, indole ring, benzisoxazole ring or benzo[b]thiophene ring, $R^4$ denotes a hydrogen atom or alkyl group with carbon atoms of 1 to 8, $X^5$ denotes an oxygen atom or sulfur atom, and $R^5$ denotes an alkyl group with carbon atoms of 1 to 8 which may have substituents, aralkyl group or aryl group), are reported.

However, these compounds have different structure from that of the inventive compounds in the points that carbonyl group or amide group is not contained in $Y^2$ and $X^4$ being connecting portions and that $W^1$ to bind to 3-position of propanoic acid is heterocycle, and it is not described that these compounds have the binding activity to human PPARα and the transcription-activating function.

As propanoic acid derivatives with blood sugar-lowering action and lipid-decreasing action, in International Publication No. WO98/07699 (Japan Tobacco Inc.), compounds represented by a general formula (C)

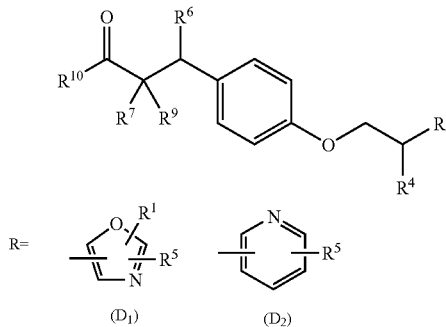

(C)

(wherein R denotes a substituent represented by $D_1$ or $D_2$, $R^1$ denotes an aromatic ring, cycloalkyl group or heteroaromatic ring, $R^5$ denotes an alkyl group, $R^4$ denotes a hydrogen atom or alkyl group, $R^6$ denotes a hydrogen atom or it may be connected to $R^9$ to form double bond, $R^7$ denotes a carboxyl group, acyl group, alkoxycarbonyl group which may have substituents, alkyl group, aryloxycarbonyl group, aralkyloxycarbonyl group, carbamoyl group, $NHR^8$ group or $OR^8$ group, $R^8$ denotes an acyl group which may have substituents or alkoxycarbonyl group, $R^9$ denotes a hydrogen atom, alkyl group or alkoxycarbonyl group, and $R^{10}$ denotes a hydrogen atom, amino group, alkoxy group, alkyl group, aryloxy group or aralkyloxy group), are reported. However, these compounds also have different structure from that of the inventive compounds in the point that substituents on benzene ring are of disubstituted form at 1-position and 4-position, and it is not described that these compounds have the binding activity to human PPARα and the transcription-activating function.

As carboxylic acid derivatives with working function on leukotriene receptor, in Japanese Unexamied Patent Publication No. Sho 63-091354 (Yamanouchi Pharmaceutical Co., Ltd.), compounds represented by a general formula (E)

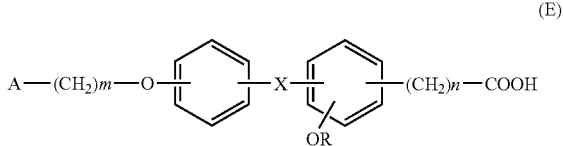

(E)

(wherein A denotes a hydrogen atom or phenyl group, m denotes an integer of 3 to 10, n denotes an integer of 1 to 6, X denotes CONH group or NHCO group, and R denotes a carboxy lower alkyl group or carboxy lower alkylcarbamoyl group (however, when A is phenyl group, R is carboxy lower alkylcarbamoyl lower alkyl group)), are reported.

However, since these compounds have no substituent at 2-position of propanoic acid and carbonyl groups exist in all of R group portions, the structure differs from that of the inventive compounds, and it is not described that these compounds have the binding activity to human PPARα and the transcription-activating function.

As carboxylic acid derivatives with antagonism against fibrinogen receptor, in U.S. Pat. No. 5,227,490 (Merck & Co., Inc.), compounds represented by a general formula (F)

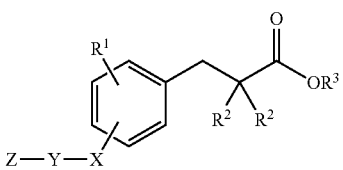

(F)

(wherein $R^1$ denotes a hydrogen atom, $C_{1-6}$ alkyl group, aryl $C_{4-10}$ alkyl group, aryl group, carboxyl group, $C_{1-6}$ alkoxy group, carboxy $C_{0-6}$ alkyl group, carboxy $C_{0-6}$ alkoxy group, hydroxy $C_{1-6}$ alkyl group, $C_{1-4}$ alkylsulfonyl $C_{0-6}$ alkyl group, $C_{0-4}$ alkylamino $C_{0-6}$ alkyl group, aryl $C_{0-10}$ alkylamino $C_{0-6}$ alkyl group, $C_{2-10}$ acylamino $C_{0-6}$ alkyl group, $C_{1-4}$ carboalkoxy $C_{0-6}$ alkyl group or halogen atom, $R^2$s denote identically or differently hydrogen atoms, halogen atoms, hydroxyl groups, $C_{1-6}$ alkoxy groups, aryl $C_{0-4}$ alkyl groups, aryl $C_{0-6}$ alkoxy groups or $C_{1-6}$ alkyl groups which may have substituents, $R^3$ denotes a hydrogen atom, $C_{1-6}$ alkyl group or aryl $C_{1-10}$ alkyl group, X denotes an oxygen atom, sulfur atom, SO group, $SO_2$ group, CO group, $NR^4CO$ group, $CONR^4$ group, $CH_2$ group, CH=CH group or $NR^4CS$ group, Y denotes a $C_{1-10}$ alkyl group which is unsubstituted or which may have substituents, $C_{4-8}$ cycloalkyl group, aryl group, $C_{0-3}$ alkylaryl $C_{0-3}$ alkyl group, $C_{0-3}$ alkylaryl $C_{0-3}$ alkylcarbonyl group, $C_{0-3}$ alkylaryl $C_{0-3}$ alkylcarboxyamide group, $C_{0-3}$ alkylaryloxy $C_{0-3}$ alkyl group, CONH group, NHCO group or $(CH_2)m$-Q-$(CH_2)_n$ group (however, Q denotes a $C_{3-8}$ membered heterocycle containing 1 to 3 kinds of heteroatoms selected from oxygen and sulfur, and m and n denote 0 to 4), and Z denotes a $NR^4R^5$ group (however, $R^4$ and $R^5$ denote identically or differently hydrogen atoms, $C_{1-6}$ alkyl groups, aryl $C_{1-10}$ alkyl groups in which alkyl group is unsubstituted or may be substituted with $C_{1-4}$ alkoxy group, carboxy $C_{0-6}$ alkyl group, hydroxyl group, halogen atom, or 4–9 membered monocyclic or bicyclic ring containing 1 to 3 heteroatoms selected from nitrogen, oxygen and sulfur) or guanidino group which may have substituents), are reported.

However, from the fact that these compounds are amino acid derivatives inevitably containing amino groups, all of which may have substituents, in Z group portion, the structure is different from that of the inventive compounds, and it is not described that these compounds have the binding activity to human PPARα and the transcription-activating function.

With respect to patents that report the working function on PPARα, compounds represented by a general formula (G)

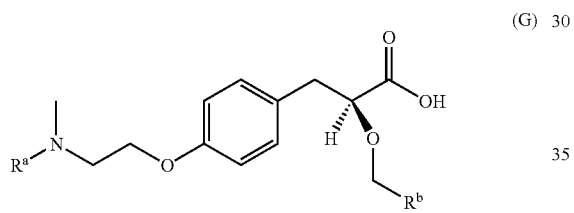

(G)

(wherein $R^a$ denotes a 2-benzoxazolyl group or 2-pyridyl group, and $R^b$ denotes a methoxymethyl group or trifluoromethyl group), are reported in International Publication No. WO97/25042 (SmithKline Beecham plc.) as compounds with working functions on PPARα and PPARγ. However, the structure of these compounds is different from that of the inventive compounds in the point that substituents on benzene ring are of disubstituted derivatives at 1-position and 4-position, and further it is not described that they have the binding activity to human PPARα and the transcription-activating function.

As compounds with working function on PPARα, in International Publication No. WO97/36579 (Glaxo Welcome Corp.), compounds represented by a general formula (H)

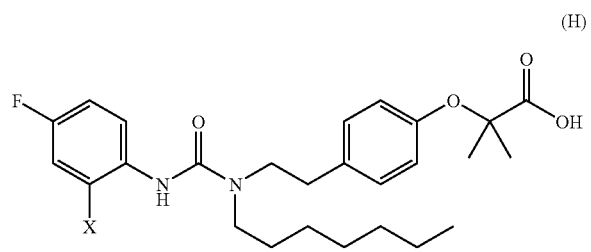

(H)

(wherein X denotes a hydrogen atom or fluorine atom), are reported.

However, the structure is different from that of the inventive compounds in the points that these compounds are phenoxyacetic acid derivatives and that the position relationship of substituents on benzene ring is of disubstituted format 1-position and 4-position. Also, the transcription-activating function of PPARα is never satisfied in strength.

With abrupt changes in the dietary habits and life style, it is a problem to increase the frequency of arteriosclerotic diseases such as ischemic heart disease. As main risk factors of these arteriosclerotic diseases, hyperlipidemia, diabetes and hypertension are being considered, and it is said that, for the pathology thereof, the existence of insulin resistance is important. Now, it has become clear that the obesity due to the accumulation of visceral fat is concerned therein as a pathogenic basis. For this reason, the development of a therapeutic drug for metabolic diseases being overall effective for these diseases and having high safety is desired clinically.

DISCLOSURE OF THE INVENTION

As a result of diligent studies paying an attention to such specific role of human PPAR, aiming at the creation of structurally novel drug with effectiveness and high safety as a therapeutic drug for metabolic diseases, the inventors have found that novel substituted carboxylic acid derivatives represented by a following general formula (1) have excellent binding activity to human PPAR and transactivation activity, leading to the completion of the invention. Namely, the invention relates to substituted carboxylic acid derivatives represented by a general formula (1)

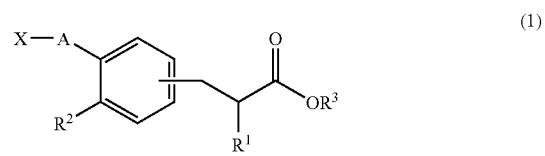

(1)

[wherein $R^1$ denotes a hydrogen atom, lower alkyl group with carbon atoms of 1 to 4 or lower alkoxy group with carbon atoms of 1 to 3, $R^2$ denotes a lower alkoxy group with carbon atoms of 1 to 3, $R^3$ denotes a hydrogen atom or lower alkyl group with carbon atoms of 1 to 4, A portion denotes a connecting mode of —NHCO—, —$CH_2$NHCO—, —CONH—, —$CH_2$CONH—, —NHCO$CH_2$— or —CONHCH$_2$—, X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group), and the substituting position of the portion of carboxylic acid residue is para position to A substituent or $R^2$ substituent], and their pharmaceutically acceptable salts and their hydrates.

The salts of the compounds represented by the general formula (1) in the invention are of common use and pharmacologically acceptable salts such as metal salts, for example, alkali metal salts (e.g. sodium salt, potassium salt, lithium salt, etc.), alkaline earth metal salts (e.g. calcium salt, magnesium salt, etc.) and aluminum salt are mentioned. Moreover, among the compounds represented by the general formula (1) and compounds obtainable in their sysnthetic processes in the invention, there exist compounds that can be converted to acid addition salts, and, as the acids in those cases, pharmacologically acceptable inorganic acids, for example, hydrochloric acid, sulfuric acid, hydrobromic acid and phosphoric acid, or organic acids, for example, maleic acid, fumaric acid, acetic acid, oxalic acid, tartaric acid, benzene-sulfonic acid, etc. are mentioned.

Moreover, the compounds represented by the general formula (1) in the invention sometimes include optical isomers based on the propionic acid portion. Moreover, compounds obtainable in the process of synthesizing the compounds represented by the general formula (1) sometimes include a mixture of geometrical isomers. Such isomers and their mixtures are all included in the scope of this invention.

Respective optical isomers can be prepared through the stereoselective synthetic process. Moreover, they can also be prepared by separating the diastereomeric ester derivatives or oxazolidinone derivatives obtainable by reacting with optically active alcohol derivatives or optically active oxazolidinone derivatives, by the technique of fractional crystallization or chromatography. Furthermore, they can also be prepared by the technique of chromatography that uses chiral support.

In the general formula (1) of the invention, for "lower alkyl group with carbon atoms of 1 to 4", straight chain or branched ones with carbon atoms of 1 to 4 such as methyl, ethyl, propyl, isopropyl and butyl are mentioned.

For "lower alkoxy groups with carbon atoms of 1 to 3", straight chain or branched ones with carbon atoms of 1 to 3 such as methoxy, ethoxy, isopropoxy and propoxy are mentioned.

For the substituents permissible in "pyridyl group which is unsubstituted or which may have substituents", lower alkyl group with carbon atoms of 1 to 4, halogen atom, etc. are mentioned.

For the substituents permissible in "pyridazinyl group which is unsubstituted or which may have substituents", halogen atom etc. are mentioned.

For "halogen atoms", fluorine atom, chlorine atom, bromine atom and iodine atom are mentioned.

Compounds represented by a general formula (1a), the connecting mode of A portion being —NHCO— or —CH$_2$NHCO—, R$^3$ being hydrogen atom, and the substituting position of the portion of carboxyl acid residue being para position to R$^2$, among the compounds of said general formula (1) can be prepared, for example, through following processes (Scheme 1).

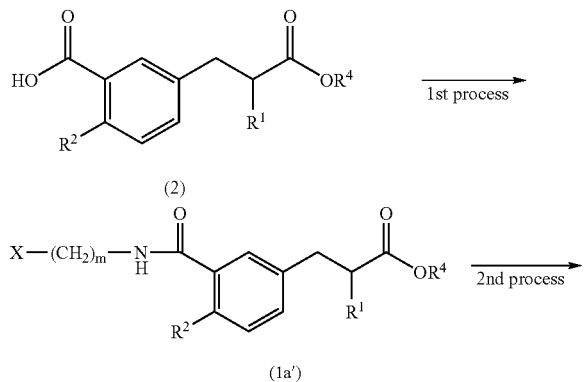

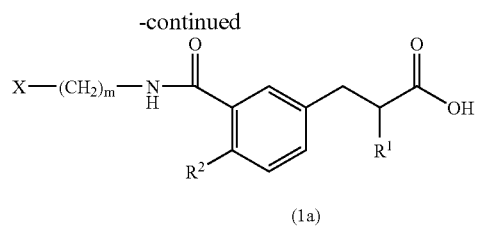

Namely, compounds represented by the general formula (1a)

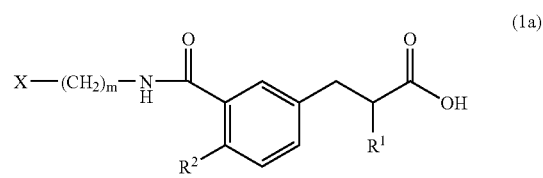

[wherein R$^1$ denotes a hydrogen atom, lower alkyl group with carbon atoms of 1 to 4 or lower alkoxy group with carbon atoms of 1 to 3, R$^2$ denotes a lower alkoxy group with carbon atoms of 1 to 3, X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group), and m denotes 0 or 1], can be prepared by reacting (first process) compounds (Jpn. Kokai Tokkyo Koho JP2001-55367) represented by a general formula (2)

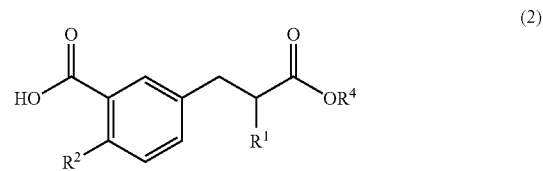

[wherein R$^1$ and R$^2$ are as described above, and R$^4$ denotes a lower alkyl group with carbon atoms of 1 to 4], with compounds represented by a general formula (3)

X—(CH$_2$)$_m$—NH$_2$ (3)

[wherein X and m are as described above], to synthesize compounds represented by a general formula (1a')

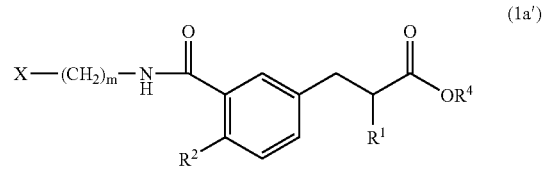

[wherein R$^1$, R$^2$, R$^4$, X and m are as described above], and by hydrolyzing (second process) the COOR$^4$ position of these compounds.

The reaction of the first process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive derivative, the reaction can be performed in a solvent such as 1,4-dioxane or N,N-dimethylformamide, in the presence or absence of base, for example, alkali metal hydride such as sodium hydride, alkali metal hydroxide such as sodium hydroxide, alkali metal carbonate such as potassium carbonate, or organic base such as pyridine or triethylamine.

In the case of conducting the reaction by leaving carboxylic acid form as it is, the reaction can be performed in a solvent such as methylene chloride, chloroform, 1,4-dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxy-benzotriazole, N-hydroxy-succinimide, 3,4-dihydro-3-hydroxy-4-oxo-1,2,3-benzotriazine or the like can be mentioned. The reaction can be performed at a reaction temperature of –20° C. to 100° C., preferably 0° C. to 50° C.

The reaction of the second process can be performed under alkaline condition. For the alkaline condition, lithium hydroxide, sodium hydroxide, potassium hydroxide, or a mixture of one of these alkali metal hydroxides with methanol, ethanol, tetrahydrofuran or the like, or the like is used. The reaction can be performed at a reaction temperature of –20° C. to 100° C., preferably 0° C. to 50° C.

Compounds represented by a general formula (1b), the connecting mode of A portion being —CONH— or —CH$_2$CONH— and R$^3$ being hydrogen atom, among the compounds of said general formula (1) can be prepared, for example, through following processes (Scheme 2).

Namely, compounds represented by the general formula (1b)

[wherein R$^1$ denotes a hydrogen atom, lower alkyl group with carbon atoms of 1 to 4 or lower alkoxy group with carbon atoms of 1 to 3, R$^2$ denotes a lower alkoxy group with carbon atoms of 1 to 3, X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group), and m denotes 0 or 1], can be prepared by reacting (third process) compounds (Japanese Patent Application No. 2000-158424) represented by a general formula (4)

[wherein R$^1$ and R$^2$ are as described above, and R$^4$ denotes a lower alkyl group with carbon atoms of 1 to 4], with compounds represented by a general formula (5)

[wherein X and m are as described above], to synthesize compounds represented by a general formula (1b')

[wherein R$^1$, R$^2$, R$^4$, X and m are as described above], and by hydrolyzing (fourth process) the COOR$^4$ position of these compounds.

The reaction of the third process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using

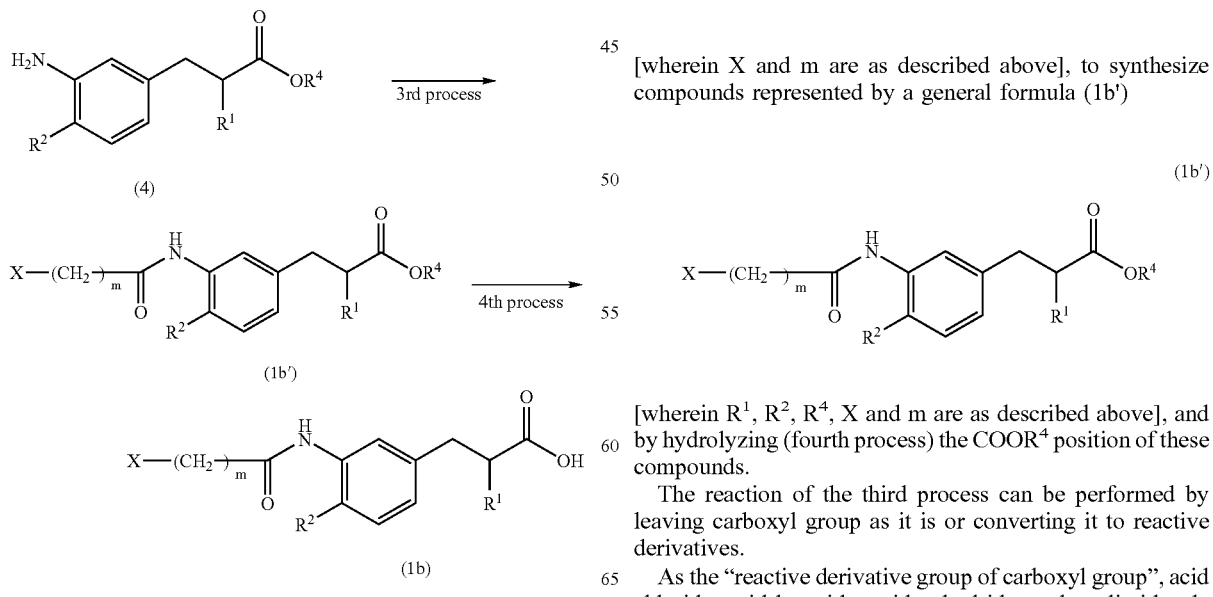

reactive derivative, the reaction can be performed in a solvent such as 1,4-dioxane or N,N-dimethylformamide, in the presence or absence of base, for example, alkali metal hydride such as sodium hydride, alkali metal hydroxide such as sodium hydroxide, alkali metal carbonate such as potassium carbonate, or organic base such as pyridine or triethylamine.

In the case of conducting the reaction by leaving carboxylic acid form as it is, the reaction can be performed in a solvent such as methylene chloride, chloroform, 1,4-dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxy-succinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The reaction of the fourth process can be performed under alkaline condition. For the alkaline condition, lithium hydroxide, sodium hydroxide, potassium hydroxide, or a mixture of one of these alkali metal hydroxides with methanol, ethanol, tetrahydrofuran or the like, or the like is used. The reaction can be performed at a reaction temperature of −20° C. to 100° C., preferably 0° C. to 50° C.

Next, compounds represented by a general formula (1c), the connecting mode of A portion being —NHCOCH$_2$— and R$^3$ being hydrogen atom, among the compounds of said general formula (1) in the invention can be prepared, for example, through following processes (Scheme 3).

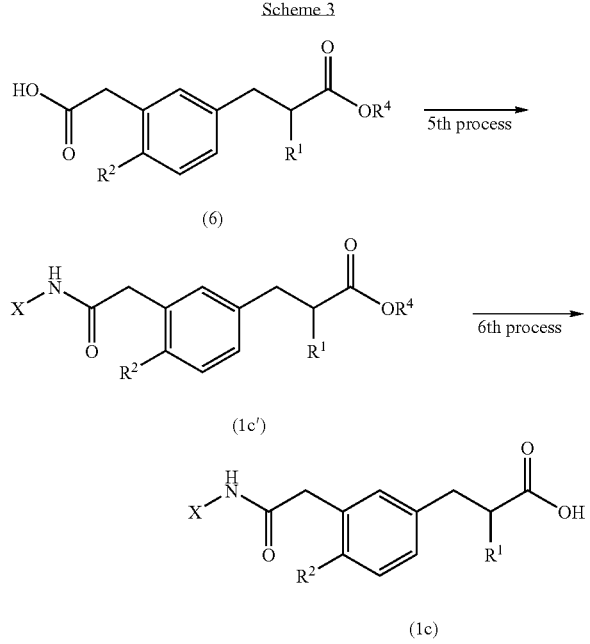

Namely, compounds represented by the general formula (1c)

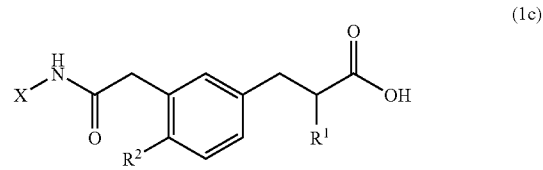

[wherein R$^1$ denotes a hydrogen atom, lower alkyl group with carbon atoms of 1 to 4 or lower alkoxy group with carbon atoms of 1 to 3, R$^2$ denotes a lower alkoxy group with carbon atoms of 1 to 3, and X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group)], can be prepared by reacting (fifth process) compounds (Japanese Patent Application No. 2000-158424) represented by a general formula (6)

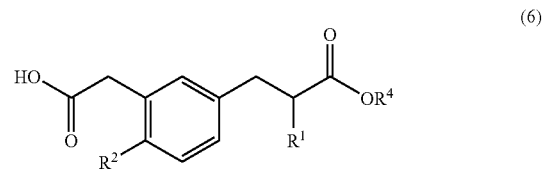

[wherein R$^1$ and R$^2$ are as described above, and R$^4$ denotes a lower alkyl group with carbon atoms of 1 to 4], with compounds represented by a general formula (7)

X—NH$_2$ (7)

[wherein X is as described above], to synthesize compounds represented by a general formula (1c′)

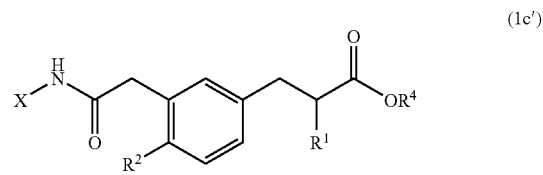

[wherein R$^1$, R$^2$, R$^4$ and X are as described above], and by hydrolyzing (sixth process) the COOR$^4$ position of these compounds.

The reaction of the fifth process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive derivative, the reaction can be performed in a solvent such as 1,4-dioxane or N,N-dimethylformamide, in the presence or absence of base, for example, alkali metal hydride such as sodium hydride, alkali metal hydroxide such as sodium hydroxide, alkali metal carbonate such as potassium carbonate, or organic base such as pyridine or triethylamine.

In the case of conducting the reaction by leaving carboxylic acid form as it is, the reaction can be performed in a solvent such as methylene chloride, chloroform, 1,4-dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The reaction of the sixth process can be performed under alkaline condition. For the alkaline condition, lithium hydroxide, sodium hydroxide, potassium hydroxide, or a mixture of one of these alkali metal hydroxides with methanol, ethanol, tetrahydrofuran or the like, or the like is used. The reaction can be performed at a reaction temperature of −20° C. to 100° C., preferably 0° C. to 50° C.

Moreover, compounds represented by a general formula (1d), the connecting mode of A portion being —CONHCH$_2$— and R$^3$ being hydrogen atom, among the compounds of said general formula (1) can be prepared, for example, through following processes (Scheme 4).

Scheme 4

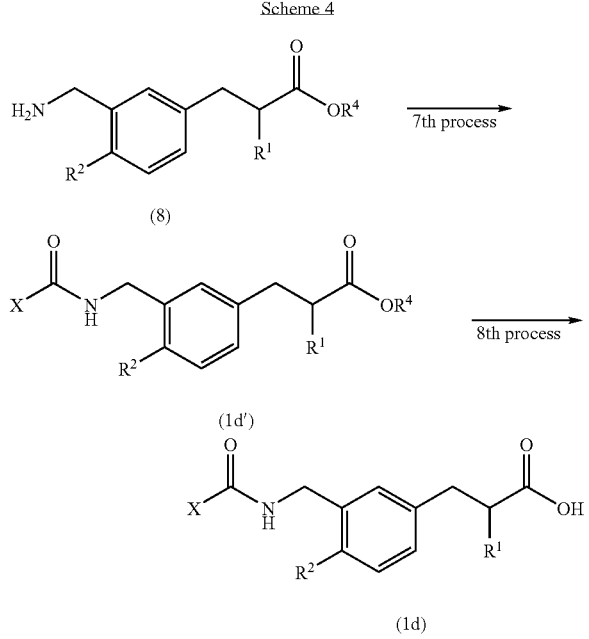

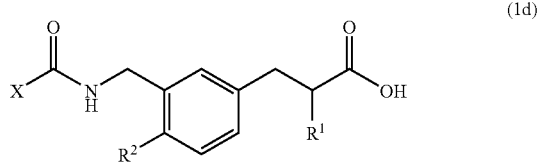

Namely, compounds represented by the general formula (1d)

(1d)

[wherein R$^1$ denotes a hydrogen atom, lower alkyl group with carbon atoms of 1 to 4 or lower alkoxy group with carbon atoms of 1 to 3, R$^2$ denotes a lower alkoxy group with carbon atoms of 1 to 3, and X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group)], can be prepared by reacting (seventh process) compounds (Japanese Patent Application No. 2000-158424) represented by a general formula (8)

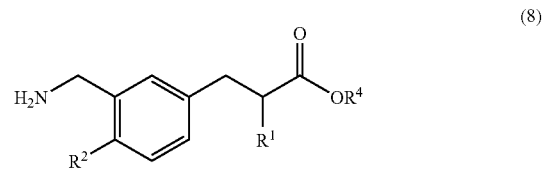

[wherein R$^1$ and R$^2$ are as described above, and R$^4$ denotes a lower alkyl group with carbon atoms of 1 to 4], with compounds represented by a general formula (9)

[wherein X is as described above], to synthesize compounds represented by a general formula (1d')

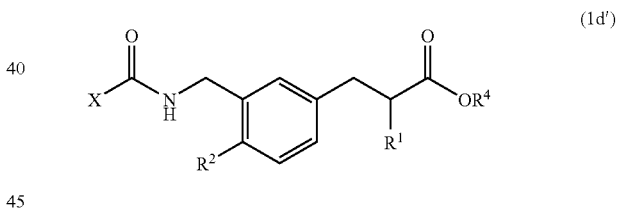

[wherein R$^1$, R$^2$, R$^4$ and X are as described above], and by hydrolyzing (eighth process) the COOR$^4$ position of these compounds.

The reaction of the seventh process can be performed by leaving carboxyl group as it is or converting it to reactive derivatives.

As the "reactive derivative group of carboxyl group", acid chloride, acid bromide, acid anhydride, carbonylimidazole or the like is mentioned. In the case of the reaction using reactive derivative, the reaction can be performed in a solvent such as 1,4-dioxane or N,N-dimethylformamide, in the presence or absence of base, for example, alkali metal hydride such as sodium hydride, alkali metal hydroxide such as sodium hydroxide, alkali metal carbonate such as potassium carbonate, or organic base such as pyridine or triethylamine.

In the case of conducting the reaction by leaving carboxylic acid form as it is, the reaction can be performed in a solvent such as methylene chloride, chloroform, 1,4-dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned.

The reaction can be performed at a reaction temperature of −20° C. to 100° C., preferably 0° C. to 50° C. The reaction of the eighth process can be performed under alkaline condition. For the alkaline condition, lithium hydroxide, sodium hydroxide, potassium hydroxide, or a mixture of one of these alkali metal hydroxides with methanol, ethanol, tetrahydrofuran or the like, or the like is used. The reaction can be performed at a reaction temperature of −20° C. to 100° C., preferably 0° C. to 50° C.

As the administering forms of novel compounds of the invention, solid compositions, liquid compositions and other compositions for oral administration, and injections, medicines for external use, suppositories, etc. for parenteral administration can be mentioned. The solid compositions for oral administration include tablets, pills, capsules, powders and granules. The liquid compositions for oral administration include pharmaceutically acceptable emulsions and syrups. The other compositions for oral administration include sprays. Moreover, the injections for parenteral administration include aseptic aqueous or nonaqueous solutions, suspensions and emulsions.

BEST EMBODIMENT TO PUT THE INVENTION INTO PRACTICE

In following, the invention will be illustrated based on concrete examples, but the invention is not confined to these examples.

EXAMPLE 1

Methyl 3-[3-[N-(3-pyridylmethyl)carbamoyl]-4-methoxyphenyl]-propionate

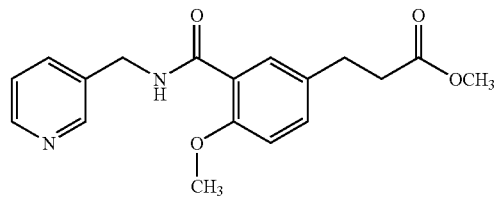

2-Methoxy-5-[(2-methoxycarbonyl)ethyl]benzoic acid (666 mg, 3.00 mmol) [Japanese Patent Application No. 2000-157600], 3-(aminomethyl)pyridine (422 mg, 3.90 mmol), triethylamine (1.04 mL, 7.50 mmol) and 30 mL of dehydrated methylene chloride were mixed, and, under cooling with ice and stirring, a solution of 2-chloro-1,3-dimethylimidazolinium chloride (711 mg, 4.20 mmol) dissolved into 20 mL of dehydrated methylene chloride was added dropwise. Next, after stirring for 30 minutes at 0° C. and for 6 hours at room temperature, the reaction mixture was washed with water and with 0.5 mol/L aqueous solution of sodium hydrogen-carbonate, then dried over anhydrous sodium sulfate and concentrated. The residue was purified by silica gel chromatography (eluate ethyl acetate) to obtain 450 mg (46%) of the title compound as a colorless oil.

Mass analysis m/z 328(M$^+$).

EXAMPLES 2 THROUGH 14

Similarly to Example 1, through the condensation reaction using 2-chloro-1,3-dimethylimidazolinium chloride, compounds shown in Table 2 were obtained.

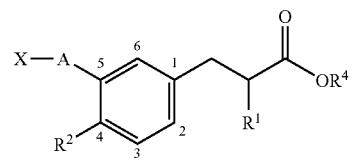

TABLE 2

| Example | R$^1$ | R$^2$ | R$^4$ | A | Substituting position of A | X | Mass analysis EI$^+$; (M/Z) |
|---|---|---|---|---|---|---|---|
| 2 | H | OCH$_3$ | CH$_3$ | CH$_2$NHCO | 1 | (2-pyridyl) | 328(M$^+$) |
| 3 | C$_2$H$_5$ | OCH$_3$ | C$_2$H$_5$ | CH$_2$NHCO | 1 | (2-pyridyl) | 371(M+H)$^{+a)}$ |

TABLE 2-continued

| Example | R¹ | R² | R⁴ | A | Substituting position of A | X | Mass analysis EI⁺; (M/Z) |
|---|---|---|---|---|---|---|---|
| 4 | $C_2H_5$ | $OCH_3$ | $C_2H_5$ | $CH_2NHCO$ | 1 | 3-methylpyridine | 371(M+H)⁺ ᵃ⁾ |
| 5 | $C_2H_5$ | $OCH_3$ | $CH_3$ | $CH_2NHCO$ | 1 | 2-(4-methylphenoxy)pyridine | 448(M⁺) |
| 6 | $C_2H_5$ | $OCH_3$ | $CH_3$ | $CH_2NHCO$ | 1 | 3-chloro-6-(4-methylphenoxy)pyridazine | 483(M⁺) |
| 7 | H | $OCH_3$ | $CH_3$ | NHCO | 1 | 2-phenoxy-5-methylpyridine | 406(M⁺) |
| 8 | $C_2H_5$ | $OCH_3$ | $CH_3$ | NHCO | 1 | 2-phenoxy-5-methylpyridine | 434(M⁺) |
| 9 | H | $OCH_3$ | $CH_3$ | $CH_2CONH$ | 2 | 3-methylpyridine | 328(M⁺) |
| 10 | $C_2H_5$ | $OCH_3$ | $C_2H_5$ | $CONHCH_2$ | 1 | 3-(4-methylphenoxy)pyridine | 462(M⁺) |
| 11 | $C_2H_5$ | $OCH_3$ | $C_2H_5$ | $NHCOCH_2$ | 1 | 3-methylpyridine | 371(M+H)⁺ ᵃ⁾ |
| 12 | $OCH_3$ | $OCH_3$ | $C_2H_5$ | $CH_2CONH$ | 1 | 3-methylpyridine | 372(M⁺) |
| 13 | $OCH_3$ | $OCH_3$ | $C_2H_5$ | $CH_2CONH$ | 1 | 4-methylpyridine | 372(M⁺) |
| 14 | $C_2H_5$ | $OC_2H_5$ | $C_2H_5$ | $CONHCH_2$ | 1 | 2-(4-methylphenoxy)pyridine | 476(M⁺) |

ᵃ⁾Ion mode FAB⁺

EXAMPLE 15

Ethyl 2-[[3-[[[4-(2-pyridyloxy)phenyl]carbonylamino]methyl]-4-methoxyphenyl]methyl]butyrate

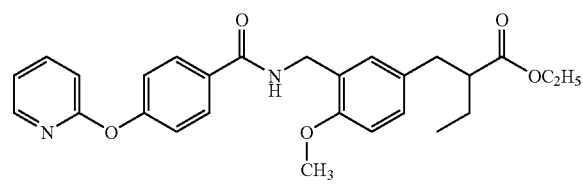

To a solution of ethyl 2-[(3-aminomethyl-4-methoxyphenyl)-methyl]butyrate hydrochloride (302 mg, 1.00 mmol) [Japanese Patent Application No. 2000-158424] and triethylamine (390 μL, 2.80 mmol) in 10 mL of dehydrated methylene chloride was added ethyl chlorocarbonate (105 μL, 1.10 mmol) under cooling with ice and stirring, and the mixture was stirred for 20 minutes under cooling with ice. Next, 4-(2-pyridyloxy)benzoic acid (237 mg, 1.10 mmol) was added and the mixture was stirred for 1 hour under cooling with ice and for 5 hours at room temperature. Methylene chloride was added to the reaction mixture, which was washed with water, brine, then dried over anhydrous sodium sulfate and concentrated. The residue was purified by silica gel chromatography (eluate n-hexane:ethyl acetate=3:2 v/v) to obtain 317 mg (68%) of the title compound as a colorless oil.

Mass analysis m/z 462(M+).

EXAMPLE 16

3-[3-[N-(3-Pyridylmethyl)carbamoyl]-4-methoxyphenyl]propionic acid

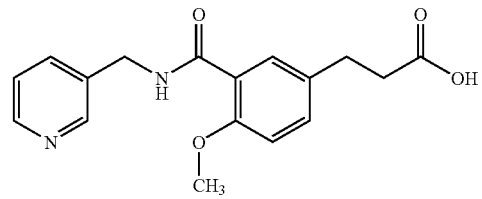

Methyl 3-[3-[N-(3-pyridylmethyl)carbamoyl]-4-methoxy-phenyl]propionate (200 mg, 0.609 mmol), 10 mL of methanol and 10 mL of 1 mol/L aqueous solution of sodium hydroxide were mixed and, after stirring for 4 hours at 60° C., the reaction mixture was concentrated under reduced pressure. The residue was neutralized with. 2 mol/L hydrochloric acid under cooling with ice. The precipitates produced were filtered and dried to obtain 90.0 mg (47%) of the title compound as colorless powder.

Melting point 175–176° C.; Mass analysis m/z 314(M+); Elemental analysis(%) $C_{17}H_{18}N_2O_4 \cdot 1/5H_2O$ (317.94): Calcd. C, 64.22; H, 5.83; N, 8.81. Found C, 64.28; H, 5.77; N, 8.68.

EXAMPLES 17 THROUGH 25

By similar technique to that in Example 16, compounds shown in Table 3 were obtained.

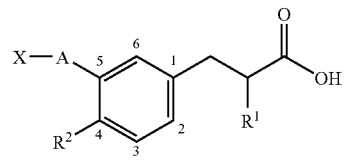

TABLE 3

| Example | $R^1$ | $R^2$ | A | Substituting position of A | X | Melting point (° C.) | Mass analysis EI+; (M/Z) | Elemental analysis (%) |
|---|---|---|---|---|---|---|---|---|
| 17 | $C_2H_5$ | $OCH_3$ | $CH_2NHCO$ | 1 | 3-pyridyl | 129–130 | 342(M+) | $C_{19}H_{22}N_2O_4 \cdot 1/5\ H_2O$ Calcd.; C 65.96, H 6.53, N 8.10 Found; C 66.07, H 6.50, N 8.08 |
| 18 | $C_2H_5$ | $OCH_3$ | $CH_2NHCO$ | 1 | 4-(2-pyridyloxy)phenyl | 138–139 | 434(M+) | $C_{25}H_{26}N_2O_5$ Calcd.; C 69.11, H 6.03, N 6.45 Found; C 68.78, H 6.13, N 6.41 |
| 19 | $C_2H_5$ | $OCH_3$ | $CH_2NHCO$ | 1 | 4-(6-chloropyridazin-3-yloxy)phenyl | foam | 469(M+) | $C_{24}H_{24}ClN_3O_5$ Calcd.; C 61.34, H 5.15, N 8.94 Found; C 61.57, H 5.44, N 8.24 |
| 20 | H | $OCH_3$ | NHCO | 1 | 5-phenoxypyridin-2-yl | 131–132 | 392(M+) | $C_{22}H_{20}N_2O_5 \cdot 1/5\ H_2O$ Calcd.; C 66.73, H 5.19, N 7.07 Found; C 66.55, H 5.15, N 7.01 |

TABLE 3-continued

| Example | R¹ | R² | A | Substituting position of A | X | Melting point (° C.) | Mass analysis EI⁺; (M/Z) | Elemental analysis (%) |
|---|---|---|---|---|---|---|---|---|
| 21 | $C_2H_5$ | $OCH_3$ | NHCO | 1 | | 59–61 | 420(M⁺) | $C_{24}H_{24}N_2O_5$ Calcd.; C 68.56, H 5.75, N 6.66 Found; C 68.18, H 5.96, N 6.55 |
| 22 | H | $OCH_3$ | $CH_2CONH$ | 2 | | 173–175 | 314(M⁺) | $C_{17}H_{18}N_2O_4$ Calcd.; C 64.96, H 5.77, N 8.91 Found; C 64.92, H 5.79, N 8.52 |
| 23 | $C_2H_5$ | $OCH_3$ | $CONHCH_2$ | 1 | | foam | 435(M+H)⁺ᵃ⁾ | $C_{25}H_{26}N_2O_5 \cdot 1/5\ H_2O$ Calcd.; C 68.54, H 6.07, N 6.39 Found; C 68.58, H 6.26, N 6.37 |
| 24 | $C_2H_5$ | $OCH_3$ | $CONHCH_2$ | 1 | | 56–58 | 434(M⁺) | $C_{25}H_{26}N_2O_5 \cdot 1/10\ H_2O$ Calcd.; C 68.82, H 6.05, N 6.42 Found; C 68.64, H 6.04, N 6.46 |
| 25 | $C_2H_5$ | $OCH_3$ | $NHCOCH_2$ | 1 | | 158–160 | 343(M+H)⁺ᵃ⁾ | $C_{19}H_{22}N_2O_4 \cdot 1/2\ H_2O$ Calcd.; C 64.94, H 6.60, N 7.97 Found; C 65.12, H 6.55, N 7.99 |

ᵃ⁾Ion mode; FAB⁺

REFERENTIAL EXAMPLE 1

2-(4-Ethoxycarbonylphenoxy)pyridine

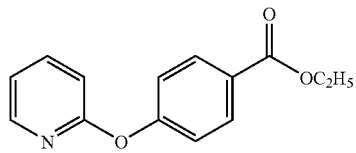

2-Bromopyridine (1.98 mL, 20.0 mmol), ethyl 4-hydroxybenzoate (6.71 g, 40.0 mmol) and potassium carbonate (2.78 g, 20.0 mmol) were mixed and the mixture was stirred for 6 hours at 150° C. to 160° C. After allowed to stand for cooling, 20 mL of 8% aqueous solution of sodium hydroxide were added to the reaction mixture, which was extracted with diethyl ether. The extracted solution was dried over anhydrous sodium sulfate and then concentrated. The residue was purified by silica gel chromatography (eluate n-hexane:ethyl acetate=10:1 v/v) to obtain 1.26 g (26%) of the title compound as a colorless oil.

Mass analysis m/z 243(M⁺).

REFERENTIAL EXAMPLE 2

4-(2-Pyridyloxy)benzoic Acid

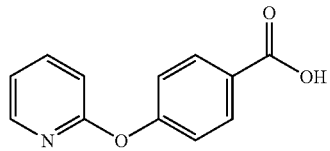

2-(4-Ethoxycarbonylphenoxy)pyridine (2.43 g, 9.99 mmol), 90 mL of ethanol and 50 mL of 1 mol/L aqueous solution of sodium hydroxide were mixed and the mixture was stirred for 3 hours at room temperature. The reaction mixture was concentrated and the residue was brought to pH3 to 4 with dilute hydrochloric acid. The precipitates produced were filtered, washed with water, and then dried to obtain 2.07 g (96%) of the title compound as colorless powder.

Mass analysis m/z 215(M⁺).

REFERENTIAL EXAMPLE 3

2-(4-Hydroxymethylphenoxy)pyridine

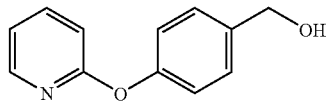

Under an atmosphere of argon, 4-(2-pyridyloxy)benzoic acid (1.08 g, 5.02 mmol) was dissolved in 20 mL of dehydrated tetrahydrofuran. Under cooling with ice and stirring, 1 mol/L borane-tetrahydrofuran complex (15.1 mL, 15.1 mmol) was added dropwise for 5 minutes and the mixture was allowed to stand overnight at room temperature. Under cooling with ice, 2 mL of 6 mol/L hydrochloric acid were added dropwise and, after stirring for 30 minutes, the reaction mixture was concentrated under reduced pressure. The residue was poured into 100 mL of ice water and, after salt was saturated, the mixture was made alkaline with potassium carbonate, which was extracted with ethyl acetate. The extracted solution was dried over anhydrous sodium sulfate and then concentrated to obtain 1.01 g (100%) of the title compound as a pale yellow oil.

¹H-NMR (400 MHz, CDCl₃) δ 4.70(2H,s), 6.92(1H,d, J=8.3 Hz), 6.99 (1H,ddd,J=7.3,4.9,1.0 Hz), 7.13(2H,d,J=8.3 Hz), 7.41(2H,d,J=8.8 Hz), 7.67–7.71(1H,m), 8.19(1H,dd, J=4.9,1.5 Hz).

REFERENTIAL EXAMPLE 4

2-[[4-(2-Pyridyloxy)phenyl]methyl]1-2,3-dihydro-1H-isoindole-2,3-dione

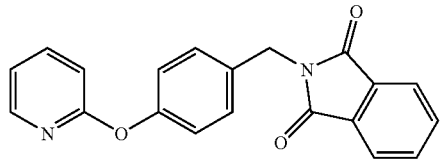

2-(4-Hydroxymethylphenoxy)pyridine (1.13 g, 5.62 mmol), phthalimide (0.928 g, 6.18 mmol), triphenylphosphine (1.69 g, 6.25 mmol) and 40 mL of dehydrated tetrahydrofuran were mixed and, after diethyl azodicarboxylate (40% toluene solution; 2.55 mL, 5.62 mmol) was added dropwise under an atmosphere of argon and under cooling with ice and stirring, the mixture was allowed to stand for 3 days at room temperature. The reaction mixture was concentrated and the residue was purified by silica gel chromatography (eluate n-hexane:ethyl acetate=2:1 v/v) to obtain 1.44 g (78%) of the title compound as colorless crystals.

Mass analysis m/z 330(M⁺).

REFERENTIAL EXAMPLE 5

2-(4-Aminomethylphenoxy)pyridine

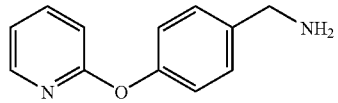

2-[[4-(2-Pyridyloxy)phenyl]methyl]-2,3-dihydro-1H-isoindole-2,3-dione (1.44 g, 4.36 mmol), hydrazine monohydrate (0.432 mL, 8.73 mmol) and 45 mL of ethanol were mixed and the mixture was refluxed for 4.5 hours. The precipitates were filtered and the filtrate was concentrated. Then, 60 mL of dehydrated tetrahydrofuran was added and, after refluxing for 2 hours, the reaction mixture was cooled to −20° C. The precipitates were filtered and water was added to the residue obtained by concentrating the filtrate, which was made alkaline with 5 mol/L aqueous solution of sodium hydroxide and then saturated with salt. Next, diethyl ether extraction was performed. The extracted solution was washed with 1 mol/L aqueous solution of sodium hydroxide, brine, then dried over anhydrous sodium sulfate and concentrated to obtain 785 mg (90%) of the title compound as a yellow oil.

Mass analysis m/z 200(M⁺).

REFERENTIAL EXAMPLE 6

3-Chloro-6-(4-formylphenoxy)pyridazine

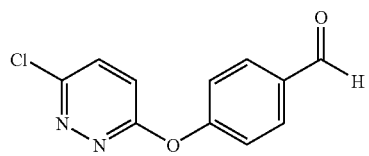

3,6-Dichloropyridazine (3.00 g, 20.1 mmol), 4-hydroxybenzaldehyde (2.46 g, 20.1 mmol), potassium carbonate (2.78 g, 20.1 mmol) and 60 mL of N,N-dimethylformamide were mixed and the mixture was refluxed for 1 hour. The reaction mixture was poured into water, which was extracted with ethyl acetate. The extracted solution was washed with brine, then dried over anhydrous magnesium sulfate and concentrated. The residue was purified by silica gel chromatography (eluate n-hexane:ethyl acetate=1:1 v/v) to obtain 4.06 g (86%) of the title compound as colorless crystalline powder.

¹H-NMR (400 MHz, CDCl₃) δ 7.25(1H,d,J=9.3 Hz), 7.39(2H,d,J=8.8 Hz), 7.56(1H,d,J=9.3 Hz), 7.96(2H,d,J=8.8 Hz), 10.01(1H,s).

REFERENTIAL EXAMPLE 7

3-Chloro-6-(4-Hydroxymethylphenoxy)pyridazine

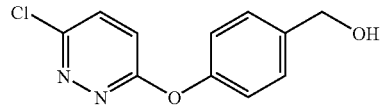

3-Chloro-6-(4-formylphenoxy)pyridazine (4.06 g, 17.3 mmol) and 200 mL of methanol were mixed, and after sodium borohydride (654 mg, 17.3 mmol) was added under cooling with ice and stirring, the mixture was stirred for 15 minutes. Water was added to the reaction mixture and methanol was distilled off. The residue was poured into water, which was extracted with ethyl acetate. The extracted solution was washed with saturated brine, then dried over anhydrous magnesium sulfate and concentrated. The residue was purified by silica gel chromatography (eluate n-hexane: ethyl acetate=1:2 v/v) to obtain 3.10 g (76%) of the title compound as a colorless oily product.

¹H-NMR (400 MHz, CDCl₃) δ 4.71(2H,s), 7.15–7.19(3, m), 7.42(2H,d,J=8.8 Hz), 7.49(1H,d,J=9.3 Hz).

REFERENTIAL EXAMPLE 8

2-[[4-[3-(6-Chloropyridazinyloxy)phenyl]methyl]-2,3-dihydro-1H-isoindole-2,3-dione

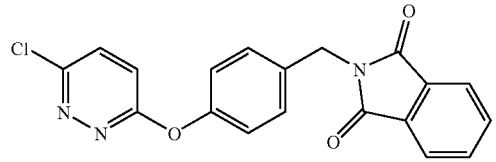

By the similar procedure to that in Referential example 4, the title compound was obtained as colorless crystalline powder.

Mass analysis m/z 365(M⁺).

REFERENTIAL EXAMPLE 9

3-(4-Aminomethylphenoxy)-6-chloropyridazine

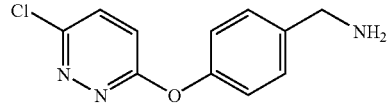

By the similar procedure to that in Referential example 5, the title compound was obtained as a dark brown oil.
Mass analysis m/z 234(M−H)+.

REFERENTIAL EXAMPLE 10

3-(4-Formylphenoxy)pyridine

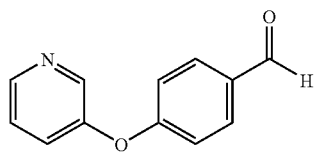

By the similar procedure to that in Referential example 6, using 3-hydroxypyridine and 4-hydroxybenzaldehyde as starting materials, the title compound was obtained as a yellow oil.
Mass analysis m/z 199(M+).

REFERENTIAL EXAMPLE 11

4-(3-Pyridyloxy)benzoic ecid

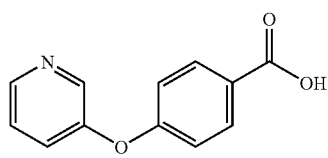

3-(4-Formylphenoxy)pyridine (2.40 g, 12.0 mmol) and 50 mL of acetone were mixed and 2.67 mol/L Jones reagent (4.00 mL, 10.7 mmol) was added under cooling with ice and stirring. After stirring for 30 minutes under cooling with ice, 2.67 mol/L Jones reagent (3.00 mL, 8.00 mmol) was added further and the mixture was stirred for 2 hours under cooling with ice. Water was added to the reaction mixture, which was neutralized with 2 mol/L aqueous solution of sodium hydroxide. Then, 100 mL of chloroform were added and the solution was filtered through celite. The insolubles were washed with hot chloroform. After the chloroform layer was separated, the aqueous layer was extracted with chloroform. Respective chloroform layers were combined and dried over anhydrous sodium sulfate, then concentrated to obtain 1.40 g (54%) of the title compound as milky white powder.
Mass analysis m/z 215(M+).

REFERENTIAL EXAMPLE 12

3-Nitro-6-phenoxypyridine

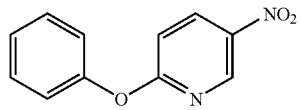

Phenol (4.10 g, 43.6 mmol) and 50 mL of 50% aqueous solution of sodium hydroxide were mixed and the mixture was stirred for 50 minutes. Next, 2-chloro-6-nitropyridine (6.90 g, 43.5 mmol), tetra-n-butylammonium chloride (1.20 g, 4.32 mmol) and 60 mL of benzene were added and the mixture was stirred for 2.5 hours at room temperature. Water was added to the reaction mixture, which was extracted with methylene chloride. The extracted solution was washed with water, then dried over anhydrous sodium sulfate and concentrated to obtain 8.77 g (93%) of the title compound as dark brown powder.
Mass analysis m/z 216(M+).

REFERENTIAL EXAMPLE 13

3-Amino-6-phenoxypyridine

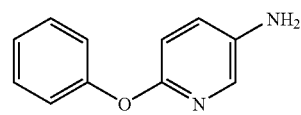

3-Nitro-6-phenoxypyridine (8.77 g, 40.6 mmol), 10% palladium on carbon (1.20 g) and 1:1 mixed solvent (250 mL) of ethyl acetate with ethanol were mixed and hydrogenation was performed at room temperature under an initial pressure of 196 kPa. After the catalyst was removed by filtration and washed with ethanol, the filtrate was concentrated. The residue was purified by silica gel chromatography (eluate n-hexane:ethyl acetate=1:1 v/v) to obtain 6.50 g (86%) of the title compound as faintly yellow needle-like crystals.
Mass analysis m/z 186(M+).

EXAMPLE 26

2-[[4-Ethoxy-3-[[[4-(2-pyridyloxy)phenyl]carbonylamino]-methyl]phenyl]methyl]butyric acid

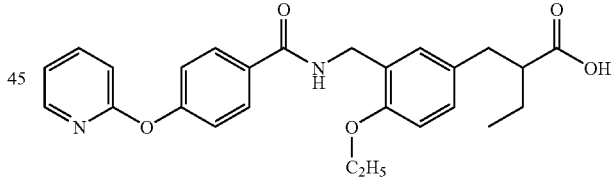

By the similar technique to that in Example 16, the title compound was obtained as a white amorphous.
$^1$H-NMR (400 MHz, CDCl$_3$) δ 0.91(3H,t,J=7.3 Hz), 1.41(3H,t,J=6.8 Hz), 1.48–1.55(1H,m), 1.58–1.67(1H,m), 2.45–2.52(1H,m), 2.67(1H,dd,J=13.7,5.9 Hz), 2.85(1H,dd, J=13.7,8.8 Hz), 4.02(2H,q,J=6.8 Hz), 4.53(2H,d,J=5.4 Hz), 6.73(1H,d,J=8.8 Hz), 6.86(1H,t,J=5.6 Hz), 6.93(1H,d,J=8.3 Hz), 7.00–7.10(2H,m), 7.11(1H,d,J=2.0 Hz), 7.18 (1H,d, J=2.0 Hz), 7.36(1H,s), 7.70(1H,dt,J=8.3, 2.0 Hz), 7.77(1H, d,J=8.8 Hz), 8.18(1H,dd,J=4.9, 2.0 Hz). High-resolution mass analysis C$_{26}$H$_{28}$N$_2$O$_5$ Calcd. 448.1998. Found 448.1996.

EXAMPLES 27 AND 28

Using a HPLC system [column: CHIRALPAK AD 1.0φ× 25 cm (DAICEL CHEMICAL INDUSTRIES, LTD.), eluate:

n-hexane:2-propanol:acetic acid=90:10:0.1, flow rate: 3.0 ml/min, temperature: 40° C., detection: UV 268 nm] with optical resolution column, compound of Example 26 being a racemic mixture was separated optically to obtain optically active compounds shown in Examples 27 and 28.

EXAMPLE 27

(+)-2-[[4-Ethoxy-3-[[[4-(2-pyridyloxy)phenyl]carbonylamino]-methyl]phenyl]methyl]butyric acid Retention time in HPLC: 66.1 min,
White amorphous,
Optical activity: dextro-rotation,
$^1$H-NMR (400 MHz, CDCl$_3$) δ 0.96(3H,t,J=7.3 Hz), 1.45(3H,t,J=6.8 Hz), 2.52–2.60(1H,m), 2.72(1H,dd,J=5.4, 13.7 Hz), 2.87(1H,dd,J=8.8, 13.7 Hz), 4.07(2H,q,J=6.8 Hz), 4.60(2H,dd,J=3.4, 5.9 Hz), 6.76(1H, brt,J=5.9 Hz), 6.78(1H, d,J=8.3 Hz), 6.96(1H,d,J=7.8 Hz), 7.02–7.07(2H,m), 7.16–7.18(3H,m), 7.70–7.75(1H,m), 7.79(2H,d,J=8.8 Hz), 8.19(1H,d,J=2.9 Hz), a CH$_2$ peak dissolved into H$_2$O.

High-resolution mass analysis C$_{26}$H$_{28}$N$_2$O$_5$ Calcd. 448.1998. Found 448.1996.

EXAMPLE 28

(−)-2-[[4-Ethoxy-3-[[[4-(2-pyridyloxy)phenyl]carbonylamino]methyl]phenyl]methyl]butyric acid Retention time in HPLC: 71.9 min,
White amorphous,
Optical activity: levo-rotation,
$^1$H-NMR (400 MHz, CDCl$_3$) δ 0.96(3H,t,J=7.3 Hz), 1.45(3H,t,J=6.8 Hz), 2.51–2.59(1H,m), 2.73(1H,dd,J=5.9, 13.7 Hz), 2.87(1H,dd,J=8.8, 13.7 Hz), 4.07(2H,q,J=6.8 Hz), 4.60(2H,dd,J=3.4,5.9 Hz), 6.7–6(1H, brt,J=5.9 Hz), 6.78 (1H,d,J=8.3 Hz), 6.96(1H,d,J=8.3 Hz), 7.02–7.07(2H,m), 7.16–7.18(3H,m), 7.70–7.74(1H,m), 7.79(2H,d,J=8.3 Hz), 8.19(1H,d,J=2.9 Hz), a CH$_2$ peak dissolved into H$_2$O. High-resolution mass analysis C$_{26}$H$_{28}$N$_2$O$_5$ Calcd. 448.1998. Found 448.1996.

UTILIZABILITY IN THE INDUSTRY

The substituted carboxylic acid derivatives represented by the general formula (1), being the inventive compounds, and their pharmaceutically acceptable salts and their hydrates have the transactivation activity on human PPAR, hence they are useful for preventive drugs for metabolic diseases such as hyperlipidemia, arteriosclerosis, diabetes and obesity.

The transactivation activity of the inventive compounds on human PPAR is confirmed by following test method.

<Test of Transactivation on Peroxisome Proliferator-Activated Receptor (PPAR)

To CHO cells cultured in a Dulbecco-modified Eagle's medium containing 10% delipidated fetal calf serum (FCS/DMEM), receptor plasmid and its reporter plasmid (STRATAGENE Corp.) that manifest fused protein of DNA-binding domain being transcription factor of yeast with each ligand-binding domain of human type PPAR (Biochemistry, 1993, 32, 5598), and luciferase plasmid of Renilla (PROMEGA Corp.) for internal standard were cotransfected with lipofectamine in the serum-free state. Thereafter, testing compound was added to the 10% SFCS/DMEM and both luciferase activities were measured after 24 hours, which were corrected with internal standard.

Results are shown in Table 1. From these results, it was shown that the inventive compounds have potent transactivation activity on PPAR.

TABLE 1

| | Transactivation activity | | |
|---|---|---|---|
| No. of example | PPARα EC$_{50}$ (μmol/L) | PPARγ EC$_{50}$ (μmol/L) | PPARδ EC$_{50}$ (μmol/L) |
| 18 | 0.14 | 9.6 | >100 |
| 23 | 0.34 | 5.4 | 2.2 |
| 26 | 0.044 | 0.41 | 0.19 |
| 27 | 0.060 | 0.55 | 0.21 |
| 28 | 0.19 | 0.58 | 1.1 |

The invention claimed is:

1. A substituted carboxylic acid compound represented by a general formula (1)

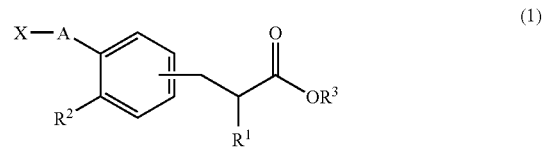

(1)

wherein R$^1$ denotes a hydrogen atom, lower alkyl group with carbon atoms of 1 to 4 or lower alkoxy group with carbon atoms of 1 to 3, R$^2$ denotes a lower alkoxy group with carbon atoms of 1 to 3, R$^3$ denotes a hydrogen atom or lower alkyl group with carbon atoms of 1 to 4, A portion denotes a connecting mode of —NHCO—, —CH$_2$NHCO—, —CH$_2$CONH—, —NHCOCH$_2$— or —CONHCH$_2$—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom and Ph denotes a phenylene group), and

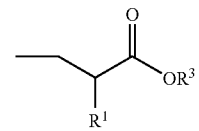

is para to A substituent or R$^2$ substituent; its pharmaceutically acceptable salt; or its hydrate.

2. A substituted carboxylic acid compound represented by a general formula (1)

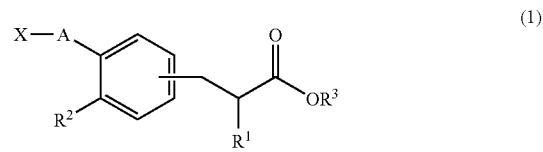

(1)

wherein $R^1$ denotes a hydrogen atom, lower alkyl group with carbon atoms of 1 to 4 or lower alkoxy group with carbon atoms of 1 to 3, $R^2$ denotes a lower alkoxy group with carbon atoms of 1 to 3, $R^3$ denotes a hydrogen atom or lower alkyl group with carbon atoms of 1 to 4, A portion denotes a connecting mode of —NHCO—, —CH$_2$NHCO—, —CONH—, —CH$_2$CONH—, —NHCOCH$_2$— or —CONHCH$_2$—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

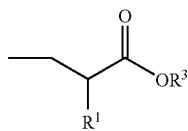

is para to A substituent or $R^2$ substituent; its pharmaceutically acceptable salt; or its hydrate, wherein $R^1$ is ethyl group.

3. A substituted carboxylic acid compound represented by a general formula (1)

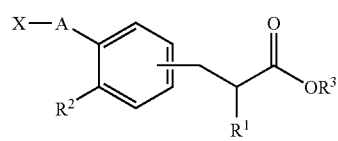

(1)

wherein $R^1$ denotes a hydrogen atom, lower alkyl group with carbon atoms of 1 to 4 or lower alkoxy group with carbon atoms of 1 to 3, $R^2$ denotes a lower alkoxy group with carbon atoms of 1 to 3, $R^3$ denotes a hydrogen atom or lower alkyl group with carbon atoms of 1 to 4, A portion denotes a connecting mode of —NHCO—, —CH$_2$NHCO—, —CONH—, —CH$_2$CONH—, —NHCOCH$_2$— or —CONHCH$_2$—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

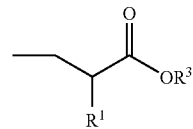

is para to A substituent or $R^2$ substituent; its pharmaceutically acceptable salts; or its hydrate, wherein $R^1$ is methoxy group.

4. A substituted carboxylic acid compound represented by a general formula (1)

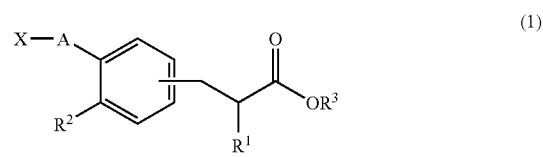

(1)

wherein $R^1$ denotes a hydrogen atom, lower alkyl group with carbon atoms of 1 to 4 or lower alkoxy group with carbon atoms of 1 to 3, $R^2$ denotes a lower alkoxy group with carbon atoms of 1 to 3, $R^3$ denotes a hydrogen atom or lower alkyl group with carbon atoms of 1 to 4, A portion denotes a connecting mode of —NHCO—, —CH$_2$NHCO—, —CONH—, —CH$_2$CONH—, —NHCOCH$_2$— or —CONHCH$_2$—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

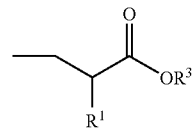

is para position to A substituent or $R^2$ substituent; its pharmaceutically acceptable salts; or its hydrate, wherein $R^2$ is methoxy group.

5. A substituted carboxylic acid compound represented by a general formula (1)

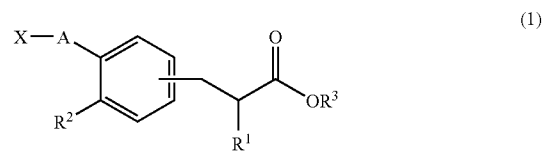

(1)

wherein R¹ denotes a hydrogen atom, lower alkyl group with carbon atoms of 1 to 4 or lower alkoxy group with carbon atoms of 1 to 3, R² denotes a lower alkoxy group with carbon atoms of 1 to 3, R³ denotes a hydrogen atom or lower alkyl group with carbon atoms of 1 to 4, A portion denotes a connecting mode of —NHCO—, —CH₂NHCO—, —CONH—, —CH₂CONH—, —NHCOCH₂— or —CONHCH₂—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

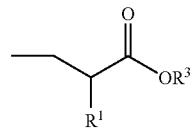

is para position to A substituent or R² substituent; its pharmaceutically acceptable salts; or its hydrate, wherein R² is ethoxy group.

6. A substituted carboxylic acid compound, its pharmaceutically acceptable salts or its hydrate of claim 1, wherein the connecting mode of A portion is —CH₂NHCO—.

7. A substituted carboxylic acid compound, its pharmaceutically acceptable salts or its hydrate of claim 1, wherein the connecting mode of A portion is —CONHCH₂—.

8. A substituted carboxylic acid compound, its pharmaceutically acceptable salts or its hydrate of claim 1, wherein X is pyridyl group which is unsubstituted or which may be substituted with lower alkyl group with carbon atoms of 1 to 4, or halogen atoms which can be fluorine, chlorine, bromine, or an iodine atom.

9. A substituted carboxylic acid compound represented by a general formula (1)

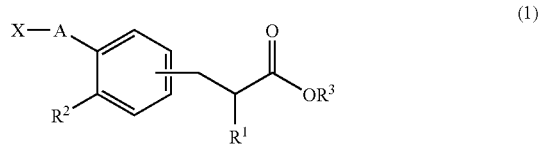

wherein R¹ denotes a hydrogen atom, lower alkyl group with carbon atoms of 1 to 4 or lower alkoxy group with carbon atoms of 1 to 3, R² denotes a lower alkoxy group with carbon atoms of 1 to 3, R³ denotes a hydrogen atom or lower alkyl group with carbon atoms of 1 to 4, A portion denotes a connecting mode of —NHCO—, —CH₂NHCO—, —CONH—, —CH₂CONH—, —NHCOCH₂— or —CONHCH₂—, X denotes a pyridyl group which is unsubstituted or which may have substituents or Y—O—Ph group (however, Y denotes a pyridyl group which is unsubstituted or which may have substituents or pyridazinyl group which is unsubstituted or which may have substituents, and Ph denotes a phenylene group), and

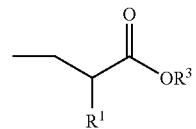

is para position to A substituent or R² substituent; its pharmaceutically acceptable salts; or its hydrate, wherein X is Y—O—Ph group (however, Y denotes a pyridyl group which is unsubstituted or which may have substituents or pyridazinyl group which is unsubstituted or which may have substituents, and Ph denotes a phenylene group).

10. A substituted carboxylic acid compound, its pharmaceutically acceptable salt, or its hydrate of claim 1, which is 2-[[3-[[[4-(2-pyridyloxy)phenyl]methyl]carbamoyl]-4-methoxyphenyl]methyl]butyric acid.

11. A substituted carboxylic acid compound, its pharmaceutically acceptable salt, or its hydrate of claim 1, which is 2-[[4-ethoxy-3-[[[4-(2-pyridyloxy)phenyl]carbonylamino]methyl]phenyl]methyl]butyric acid.

12. A substituted carboxylic acid compound, its pharmaceutically acceptable salt, or its hydrate of claim 1, which is 2-[[3-[[[4-(3-pyridyloxy) phenyl]carbonylamino]methyl]-4-methoxyphenyl]methyl]butyric acid.

13. A substituted carboxylic acid compound, its pharmaceutically acceptable salt, or its hydrate of claim 1, which is (+)-2-[[4-ethoxy-3-[[[4-(2-pyridyloxy)phenyl]carbonylamino]methyl]phenyl]methyl]butyric acid.

14. A substituted carboxylic acid compound, its pharmaceutically acceptable salt, or its hydrate of claim 1, which is (−)-2-[[4-ethoxy-3-[[[4-(2-pyridyloxy)phenyl]carbonylamino]methyl]phenyl]methyl]butyric acid.

15. A composition comprising at least one substituted carboxylic acid compound, its pharmaceutically acceptable salt, or its hydrate, of claim 1, and a pharmaceutically acceptable carrier.

16. A method comprising administering to a patient with arteriosclerosis an effective amount of at least one substituted carboxylic acid compound, its pharmaceutically acceptable salt, or its hydrate, wherein the substituted carboxylic acid compound is represented by a general formula (1)

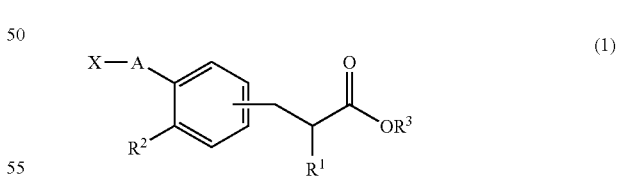

wherein R¹ denotes a hydrogen atom, lower alkyl group with carbon atoms of 1 to 4 or lower alkoxy group with carbon atoms of 1 to 3, R² denotes a lower alkoxy group with carbon atoms of 1 to 3, R³ denotes a hydrogen atom or lower alkyl group with carbon atoms of 1 to 4, A portion denotes a connecting mode of —NHCO—, —CH₂NHCO—, —CONH—, —CH₂CONH—, —NHCOCH₂— or —CONHCH₂—, X denotes a pyridyl group which is unsubstituted or which may be substituted with lower alkyt group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyt group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

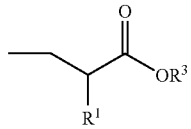

is para position to A substituent or R² substituent.

17. A method comprising administering to a patient with diabetes an effective amount of at least one substituted carboxylic acid compound, its pharmaceutically acceptable salt, or its hydrate, wherein the substituted carboxylic acid compound is represented by a general formula (1)

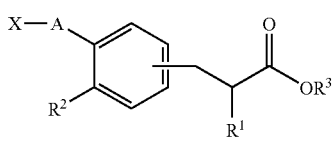

(1)

wherein R¹ denotes a hydrogen atom, lower alkyl group with carbon atoms of 1 to 4 or lower alkoxy group with carbon atoms of 1 to 3, R² denotes a lower alkoxy group with carbon atoms of 1 to 3, R³ denotes a hydrogen atom or lower alkyl group with carbon atoms of 1 to 4, A portion denotes a connecting mode of —NHCO—, —CH₂NHCO—, —CONH—, —CH₂CONH—, —NHCOCH₂— or —CONHCH₂—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

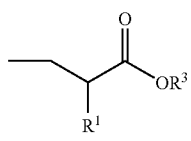

is para position to A substituent or R² substituent.

18. A substituted carboxylic acid compound represented by a general formula (1)

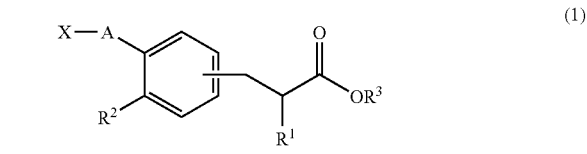

(1)

wherein R¹ denotes a hydrogen atom, lower alkyl group with carbon atoms of 1 to 4 or lower alkoxy group with carbon atoms of 1 to 3, R² denotes a lower alkoxy group with carbon atoms of 1 to 3, R³ denotes a hydrogen atom or lower alkyl group with carbon atoms of 1 to 4, A portion denotes a connecting mode of —CONH—, X denotes a pyridyl group which is unsubstituted or which may be substituted with lower alkyl group with carbon atoms of 1 to 4, or halogen atoms which can be fluorine, chlorine, bromine, or an iodine atom or Y—O—Ph group (however, Y denotes a pyridyl group which is unsubstituted or which may be substituted with lower alkyl group with carbon atoms of 1 to 4, or halogen atoms which can be fluorine, chlorine, bromine, or an iodine atom or pyridazinyl group which is unsubstituted or which may be substituted with a halogen atom which can be a fluorine, chlorine, bromine or an iodine atom, and Ph denotes a phenylene group), and

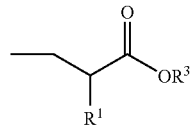

is para position to A substituent or R² substituent; its pharmaceutically acceptable salts; or its hydrate.

19. A substituted carboxylic acid compound, their pharmaceutically acceptable salts or their hydrate of claim 18, wherein X is pyridyl group which is unsubstituted or which may be substituted with lower alkyl group with carbon atoms of 1 to 4, or halogen atoms which can be fluorine, chlorine, bromine, or an iodine atom.

20. A composition comprising at least one substituted carboxylic acid compound, its pharmaceutically acceptable salt, or its hydrate, of claim 18, and a pharmaceutically acceptable carrier.

* * * * *

UNITED STATES PATENT AND TRADEMARK OFFICE
CERTIFICATE OF CORRECTION

PATENT NO. : 7,176,204 B2 Page 1 of 1
APPLICATION NO. : 10/433153
DATED : February 13, 2007
INVENTOR(S) : Miyachi et al.

It is certified that error appears in the above-identified patent and that said Letters Patent is hereby corrected as shown below:

On the title page, Item (73), the Assignee information is incorrect. Item (73) should read:

-- (73) Assignee: Kyorin Pharmaceutical Co., Ltd.,
 Tokyo (JP) --

Signed and Sealed this

Tenth Day of April, 2007

JON W. DUDAS
*Director of the United States Patent and Trademark Office*